US012778675B2

(12) United States Patent
Jones

(10) Patent No.: US 12,778,675 B2
(45) Date of Patent: Nov. 3, 2026

(54) SKIN TREATMENT DEVICE

(71) Applicant: iPulse Limited, Swansea (GB)

(72) Inventor: Stuart Terry Jones, Swansea (GB)

(73) Assignee: iPulse Limited, Swansea (GB)

( * ) Notice: Subject to any disclaimer, the term of this patent is extended or adjusted under 35 U.S.C. 154(b) by 311 days.

(21) Appl. No.: 18/421,495

(22) Filed: Jan. 24, 2024

(65) Prior Publication Data

US 2024/0261022 A1 Aug. 8, 2024

(30) Foreign Application Priority Data

Feb. 8, 2023 (GB) ...................................... 2301777

(51) Int. Cl.
*A61B 18/18* (2006.01)
*A61B 18/00* (2006.01)
*A61N 5/06* (2006.01)

(52) U.S. Cl.
CPC ............ *A61B 18/18* (2013.01); *A61N 5/0616* (2013.01); *A61B 2018/00005* (2013.01);
(Continued)

(58) Field of Classification Search
None
See application file for complete search history.

(56) References Cited

U.S. PATENT DOCUMENTS 8,882,752 B2 * 11/2014 Aharon ................ A61B 18/203 607/90
2005/0045189 A1 * 3/2005 Jay ....................... A61N 5/0617 128/898

(Continued)

FOREIGN PATENT DOCUMENTS

CN 211243681 U 8/2020
GB 2604876 A 9/2022

(Continued)

OTHER PUBLICATIONS

Extended Search Report pursuant to Rule 62 EPC in EP Application No. 24151144.3 (with priority upon on UK Patent Application No. GB2301777.5), dated Jun. 10, 2024.

(Continued)

*Primary Examiner* — Manolis Pahakis
(74) *Attorney, Agent, or Firm* — Troutman Pepper Locke LLP; Ryan A. Schneider; Nicholas H. Doss

(57) ABSTRACT

The skin treatment device that generates high intensity pulses of broadband light and includes a body, a light source to deliver light energy pulses, a control system to control the light source to deliver the light energy pulses, a primary lightguide including a solid material defining a first skin contact surface for guiding light energy to the skin of a subject, a cooling arrangement to cool the solid material, and a head configured to be mountable and demountable to the body. The device is operable in a first operable configuration with the head demounted from the body and a second operable configuration where the head is mounted to the body. In the second operable configuration, the first skin contact surface is spaced apart from the subject's skin and the light energy pulses pass through both the solid material and a light energy pulse transmission channel of a secondary lightguide.

22 Claims, 5 Drawing Sheets

(52) U.S. Cl.
CPC ............... *A61B 2018/00172* (2013.01); *A61B 2018/00476* (2013.01); *A61B 2018/00642* (2013.01); *A61B 2018/00708* (2013.01); *A61B 2018/00791* (2013.01); *A61B 2018/1807* (2013.01); *A61N 5/0617* (2013.01)

(56) References Cited

U.S. PATENT DOCUMENTS

| | | | | |
|---|---|---|---|---|
| 2007/0038206 | A1* | 2/2007 | Altshuler | A46B 15/0036 606/20 |
| 2007/0239142 | A1 | 10/2007 | Altshuler et al. | |
| 2013/0178919 | A1* | 7/2013 | McNeill | A61N 5/0616 607/90 |
| 2016/0374758 | A1 | 12/2016 | Jones et al. | |
| 2021/0178182 | A1* | 6/2021 | Palero | A61B 18/203 |
| 2022/0346871 | A1* | 11/2022 | Duan | A61B 18/18 |

FOREIGN PATENT DOCUMENTS

| | | | |
|---|---|---|---|
| WO | 2022082837 | A1 | 4/2022 |
| WO | 2022195267 | A1 | 9/2022 |

OTHER PUBLICATIONS

UKIPO Search Report from Application No. GB2301777.5 dated Jul. 18, 2023.

* cited by examiner

SKIN TREATMENT DEVICE

CROSS-REFERENCE TO RELATED APPLICATIONS

This application claims the benefit of GB Patent Application No. 2301777.5 filed 8 Feb. 2023, the entire content and substance of which is incorporated herein by reference in its entirety as if fully set forth below.

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

SEQUENCE LISTING

Not Applicable

STATEMENT REGARDING PRIOR DISCLOSURES BY THE INVENTOR OR A JOINT INVENTOR

Not Applicable

BACKGROUND OF THE DISCLOSURE

1. Field of the Invention

The present invention relates to a skin treatment device, preferably an Intense Pulsed Light (IPL) hair removal device for generation of high intensity pulses of broadband light.

2. Description of Related Art

The light pulses are typically generated by discharging the electrical energy stored in a capacitor through a xenon flashlamp delivering light energy in the form of pulses. The light from the lamp is passed through a filter to remove potentially harmful wavelengths in the ultraviolet and blue region. The light is then directed onto an area of skin for treatment. The light energy that is emitted from the device and thus reaches the skin is called the 'light output energy'.

For an IPL device using a flashlamp, the conversion of stored electrical energy into light output energy generally has an efficiency of between 20% and 40%. The remaining 60% to 80% of the energy becomes waste heat generated directly by the lamp and electronics and within the components in the light path (e.g., lightguides, filter) due to absorption (i.e., reflective or transmissive losses). Therefore:

$$\text{Electrical Energy used (per light energy pulse emitted)} = \text{Light Energy Output (per light energy pulse emitted)} + \text{Waste Heat}$$

As an approximation, it will be assumed that an IPL device using a xenon flashlamp has an efficiency of 25%. That is, the ratio of Waste Heat/Light Energy Output is 3/1.

Furthermore, Optical Power (in Watts) can be defined as:

$$\text{Optical Power} = \text{Light Output Energy per flash/Time between flashes}$$

Therefore, for the example provided, the Waste Heat Power (in Watts) is:

$$\text{Waste Heat Power} = 3 * \text{Optical Power}$$

It is generally beneficial for an IPL device to have a relatively high optical power. A higher optical power allows the device to deliver efficacious levels of energy per flash at a higher flash rate. This means that a device with higher optical power can treat a given area of skin more quickly and/or effectively than a device with lower optical power. This is particularly useful for body areas that have a large area to be treated such as legs, chest or back. From these power equations and the illustrative values, it can be understood that the higher the energy per flash, and/or the faster the device flash rate, the larger the amount of waste heat generated per second (waste heat power).

This creates a problem in IPL devices as the waste heat must be removed to prevent damage to the device itself or burn the user. This waste heat generated by the device is therefore typically removed by a forced air cooling system. This includes a small electric fan in the device that draws ambient air into the device, directing it over hot internal components (e. g. lamp, reflector etc.) before exhausting the air back out of the handset. The heat removal capacity of the forced air cooling system must be designed to match or exceed the waste heat power of the device to prevent overheating of the handset components.

Due to the requirement to ensure that the light energy pulses are actually delivered to the skin and that stray optical radiation should be minimized to avoid unsafe levels for eyes, the device should be in contact with the skin (or imperceptibly close). Stray optical radiation can be defined as light emitted by the light source that is intended to be absorbed by the target skin arca for treatment purposes, but either misses the intended target or is reflected or remitted from the target. This has a problem in that waste heat will be transferred from the device to the skin. Accordingly, how the device contacts the skin must be carefully considered. There are two main types of skin contact configuration in existing devices.

Type 1—Non-Contact—Hollow Light Pipe

The light energy pulse emitted by the lamp is filtered and then transmitted to the skin through a hollow 'light pipe' which is typically made from a thin reflective aluminum material wall defining a tube/channel which sits between the filter and the skin. The light pipe tube is hollow and therefore, the light energy pulses generated by the lamp pass through the air inside the light pipe until it hits the skin. The benefits of this arrangement are firstly aluminum light pipes are cheap to manufacture. Secondly, since the light passes through air to hit the skin, there is no solid medium in the direct light energy transfer pathway in contact with the skin to get hot due to transmission losses, and therefore no need for a complex cooling arrangement to ensure the skin contacting material remains cool.

Such Type 1 devices are capable of emitting relatively high optical power, typically in the order of 20 W, meaning larger areas of the body such as legs or the back can be treated relatively quickly as the pulse repetition rate is high. Such Type 1 devices are less beneficial however for body areas that are small and more sensitive to heat such as underarms and bikini areas. Accordingly, Type 2 devices are available.

Type 2—Contact—Solid Lightguide

The light generated by the lamp is filtered and then transmitted to the skin through a solid lightguide that contacts the skin when in operation. The lightguide is typically made from a transparent material such as glass or sapphire.

The solid lightguide material will heat up due to transmission losses and conduction during each discharge of a light energy pulse. If the solid lightguide is not specifically cooled, it may eventually reach a temperature that is painful or harmful to the skin. Therefore, a solid lightguide is typically used in combination with a thermoelectric cooling system (TEC) to extract heat from the lightguide to keep it cool which can also act to provide a cooling effect to the skin below normal skin temperature. This TEC system adds additional cost, complexity, size and weight to the device. The thermoelectric device itself also creates additional waste heat which must be exhausted by the forced air cooling system.

The higher the optical power of the device, the higher the waste heat input to the solid lightguide and therefore, the higher the TEC power required to keep the lightguide cool, adding even greater levels of cost, bulk, and complexity to the device. Typical Type 2 devices emit a maximum optical power of 8 W. The power, size and cost of the TEC system must increase proportionally to the optical power. Therefore, for a given optical power, a Type 2 device would be larger, heavier and more expensive than a Type 1 device. However, solid lightguides do have a significant benefit in that they may have a high transmission efficiency and importantly can be cooled to a temperature below normal skin temperature. This cools the surface of the skin being treated which makes the treatment safer and less painful. This is particularly helpful on more sensitive areas such as underarms and bikini areas.

It is therefore apparent that Type 1 (non-contact) devices are better suited to higher optical power devices making treatment fast for a given treatment fluence and are therefore better at treating larger body areas such as legs or backs. A Type 2 (contact) system is better suited to treatment of sensitive areas (such as underarms and bikini areas) as the sapphire lightguide can be cooled to a temperature below skin temperature. This cools the surface of the skin during treatment making the treatment less painful.

It is notable that the most sensitive body areas to be treated (underarms and bikini area) are relatively small and therefore the lower power and speed of the Type 2 system for these areas is not a significant issue.

Multiple devices are therefore required to allow the beneficial effects of Type 1 and Type 2 treatment; however, this is impractical, expensive and mostly not viable, particularly for home-use applications.

What is needed, therefore, are systems and methods that address these problems or at least provide a useful alternative.

BRIEF SUMMARY OF THE INVENTION

According to an exemplary embodiment of the present invention, a skin treatment device for delivery of light energy pulses to a subject's skin comprises a body, a light source housed within the body for discharging light energy pulses, a control system for controlling delivery of the light energy pulses, a primary lightguide for guiding light energy from the light source to the skin of a subject, the primary lightguide comprising a solid material through which the light energy pulses are transmitted, the solid material defining a first skin contact surface for providing contact with a subject's skin, a cooling arrangement for cooling the solid material, and a head configured to be mountable and demountable to the body, the head comprising a rearward end for releasably mounting to the body and extending to a forward end comprising a second skin contact surface, the head further comprising a secondary lightguide defining a light energy pulse transmission channel extending between the forward end and rearward end with the second skin contact surface defining an opening to the light energy pulse transmission channel, where the second skin contact surface extends around at least a part of the periphery of the opening.

Preferably, the device is operable in a first operable configuration with the head demounted from the body and a second operable configuration where the head is mounted to the body such that in the second operable configuration the first skin contact surface is spaced apart from the subject's skin and the light energy pulses pass through both the solid material of the primary lightguide and the light energy pulse transmission channel of the secondary lightguide.

The preferable device therefore combines the benefits of a Type 1 system (high power, speed) in the second operable configuration and a Type 2 system (safety and low pain) in the first operable configuration, without a corresponding increase in size, cost and weight, and with a simple re-configuration by a user.

With the head mounted onto the body, the head spaces the primary skin contact surface away from the skin thereby defining a secondary lightguide between the primary skin contact surface and the second skin contact surface (defined by a leading edge of the head). Accordingly, with the head mounted to the body, the primary skin contact surface is rearwardly of the second skin contact surface.

The second skin contact surface of the head beneficially defines an output window. The second skin contact surface is preferably defined by a peripheral rim extending around an opening into the secondary lightguide.

It will be appreciated by those of skill in the art that in the mounted configuration a light energy transfer pathway from the light source to the forward end (and therefore onto the skin) is through the primary and secondary lightguides.

It will be appreciated by those of skill in the art that in the second operable configuration the secondary lightguide is defined by the head and light energy is guided from the skin contact surface of the solid material of the primary lightguide toward the skin.

The device is beneficially configured to detect whether the head is mounted or demounted from the housing. A detector is beneficially provided. The detector is beneficially the control system configured to determine communication with a microprocessor in the head.

The light energy pulse transmission channel preferably comprises a bore extending from the opening towards the rearward end. The bore may extend the entire way from the opening to the rearward end.

The cooling arrangement is beneficially a Thermoelectric Cooling System (TEC). The cooling system may be only operable in the first operable configuration due to the separation of the first skin contact surface from the skin in the second operable configuration meaning cooling of the first skin contact surface is unnecessary. The TEC preferably comprises a thermoelectric cooler, a heat exchanger and a heat pipe therebetween, the TEC further comprising a fan for directing air towards the heat exchanger.

The device is preferably configured to detect whether the head is mounted or demounted from the housing, and where the control system is configured to modify operation of the skin treatment device dependent on the whether the head is mounted or demounted from the housing.

The control system is preferably configured to control delivery of multiple light energy pulses and to control delivery of an optical power output, the control system being further configured to cause modification to the optical power output dependent upon whether the head is mounted or demounted from the housing, where the optical power output is defined as light output energy per pulse emitted from the device divided by the time between consecutive pulses. The value of the optical power output is therefore beneficially modified. The device is preferably capable of modifying operation of the device without user input. This provides a safety benefit to the user. The control system can therefore modify how the device operates dependent upon whether the head is mounted to the body. The optical power output is preferably greater when the head is mounted to the body, wherein the optical power may be between 1.5-3 times greater when the head is mounted to the body.

The control system is preferably configured to control delivery of multiple light energy pulses, and the control system is further configured to control a time period between delivery of consecutive pulses and select the time period from a plurality of different time periods dependent upon whether the head is mounted or demounted form the body.

The time period is preferably less longer when the head is demounted from the housing. This means that with the head mounted to the housing, the light energy pulse repetition rate is higher. Accordingly, a user of the device will be able to treat larger body areas faster with the head mounted to the body.

It will be appreciated by those of skill in the art that the optical power output can be modified by modifying the light output energy per pulse. Light energy pulses are typically emitted by discharging a capacitor over the light energy source. By modifying the voltage on the capacitor for example the light output energy emitted by the light source can be modified.

With the head mounted and thus in the second operable configuration a higher optical power output, for example of 20 W results in a period between delivery of light energy pulses of 0.9 seconds when the total light energy output is 18 J. With the head removed in the first operable configuration the optical power output is for example 6 W, which would result in a period between delivery of light energy pulses of three seconds when the total light energy output is 18 J. For these illustrative values, if the primary and secondary lightguides have a cross sectional area of 3 $cm^2$, then a total energy is output of 18 J, giving a fluence of 6 $J/cm^2$. A typical pulse duration for an IPL hair removal device with this fluence level is in the range 0.5 msec to 2.5 msec.

The device preferably further comprises a user input trigger switchable between a deactivated and activated configuration, the activated configuration for activating discharge of the light energy pulses, where the control system is configured such that maintaining the user input trigger in an activated position causes discharge of multiple light energy pulses at a pulse repetition frequency. The device is therefore operable in different ways depending on a user input. If a user depresses and holds the user input trigger light energy pulses are emitted consecutively at the maximum permitted repetition rate controlled by the control system. Single pulses may also be emitted if the user input trigger is depressed and released where release occurs before the time period for a consecutive pulse to be emitted is reached. A consecutive pulse can then be emitted when the user input trigger is depressed again, providing that the time period has been met.

It will be appreciated by those of skill in the art that in the second operable configuration the primary and secondary lightguide combined define at least part of the pathway for light energy pulses from the light source to the skin of a subject.

It will be appreciated by those of skill in the art that the solid material of the primary lightguide can transmit light therethrough. The solid material of the primary lightguide preferably comprises glass or sapphire.

The light energy pulse transmission channel of the secondary lightguide preferably comprises a through-bore, where preferably the whole of the light energy pulse transmission channel is a through-bore. The light energy pulse transmission channel is preferably defined by a channel wall, where the channel comprises an airgap. The channel wall guides light energy pulses through the channel and is beneficially reflective. The secondary lightguide is beneficially a hollow lightguide. An alternative equivalent terminology is that the secondary lightguide is a light pipe. The channel wall may comprise aluminum.

The material of the primary lightguide may not extend the entirety of the distance between the light source and the skin contact surface. Accordingly, there may be a gap between the light source and the material. The primary lightguide preferably further comprises a filter for filtering out predetermined wavelengths of light energy. The filter preferably has a cut-on value in the range of 470 to 650 nm. The filter may comprise a coating on the solid material. Alternatively, the filter may comprise a distinct and separate component to the solid material intermediate the light source and the solid material.

The device preferably further comprises a temperature sensor configured to measure the temperature of the solid material of the primary lightguide, and where the control system is configured to control operating parameters of the cooling arrangement dependent upon the measured temperature. The control system is preferably configured to reduce the optical power output if the measured temperature reaches or exceeds a threshold value. The control system may be configured to prevent delivery of a light energy pulse if the measured temperature reaches or exceeds a threshold value.

The cooling arrangement is preferably activated in both first and second operable configurations. The cooling arrangement may be operated in a reduced power mode in the second operable configuration.

The head preferably comprises a plurality of sensors disposed adjacent the opening, where in the second operable configuration the control system is configured to receive sensor outputs from the plurality of sensors and based on the sensor outputs control operation of the device.

The body preferably comprises a plurality of sensors disposed adjacent the first skin contact surface where in the first operable configuration the control system is configured to receive sensor outputs from the plurality of sensors and based on the sensor outputs control operation of the device. The plurality of sensors disposed adjacent the first skin contact surface are either hidden by the head or are inoperable in the in the second operable configuration with the head mounted to the body.

Controlling operation of the device may comprise one or both of determining whether or not the flashlamp can emit a light energy pulse and determining properties of that pulse (e.g., fluence).

The device may comprise an adaptor for securing to the body arranged to partially obscure the first skin contact surface. This enables ease of use for treatment of smaller body areas.

At least a portion of the forward end of the head comprising the second skin contact surface is preferably at least partially moveable from a rest position to a deflected position to accommodate the geometry of the skin.

The light source is beneficially a flashlamp, preferably a xenon flashlamp.

The skin treatment device is beneficially a handheld skin treatment device. The body is beneficially configured to be grasped by a user.

These and other aspects of the present invention are described in the Detailed Description below and the accompanying figures. Other aspects and features of embodiments of the present invention will become apparent to those of ordinary skill in the art upon reviewing the following description of specific, exemplary embodiments of the present invention in concert with the figures. While features of the present invention may be discussed relative to certain embodiments and figures, all embodiments of the present invention can include one or more of the features discussed herein. Further, while one or more embodiments may be discussed as having certain advantageous features, one or more of such features may also be used with the various embodiments of the invention discussed herein. In similar fashion, while exemplary embodiments may be discussed below as device, system, or method embodiments, it is to be understood that such exemplary embodiments can be implemented in various devices, systems, and methods of the present invention.

BRIEF DESCRIPTION OF THE DRAWINGS

The accompanying drawings, which are incorporated in and constitute a part of this specification, illustrate multiple embodiments of the presently disclosed subject matter and serve to explain the principles of the presently disclosed subject matter. The drawings are not intended to limit the scope of the presently disclosed subject matter in any manner.

DETAILED DESCRIPTION OF THE INVENTION

Figure 1A:
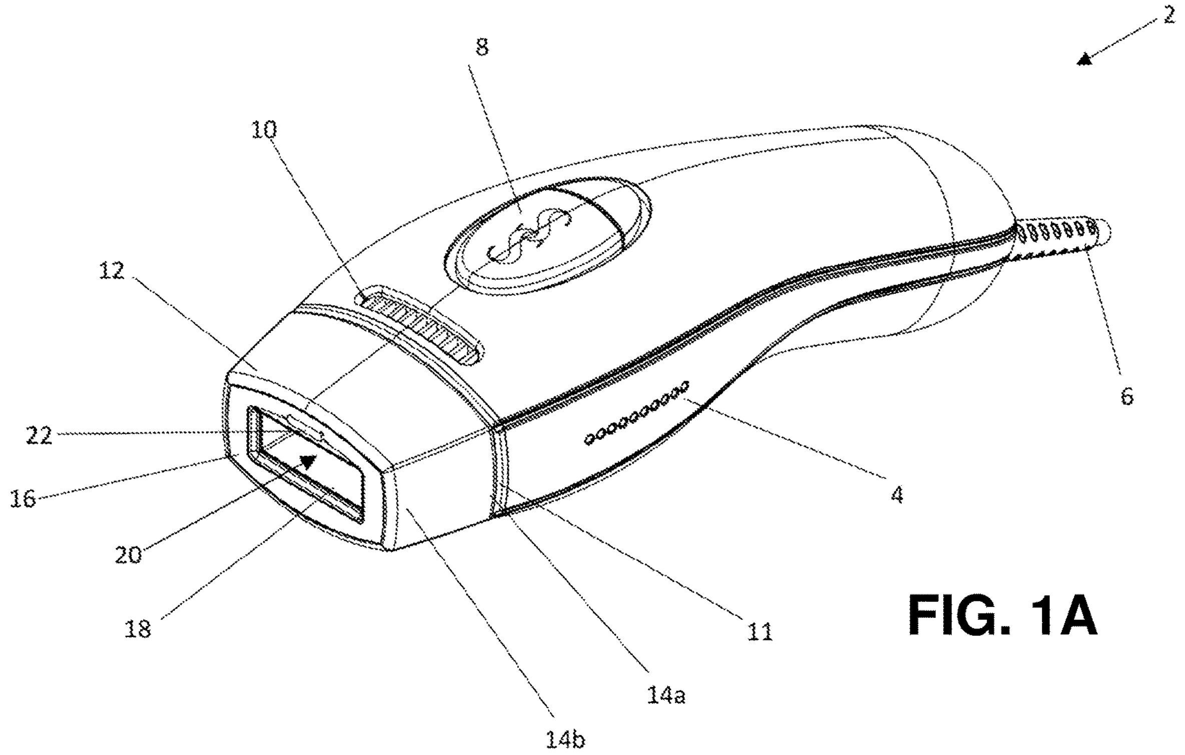
FIGS. 1A, 1B are schematic perspective views of a device according to an illustrative embodiment of the present invention with a head attached in FIG. 1A and detached in FIG. 1B.

Although certain embodiments of the disclosure are explained in detail, it is to be understood that other embodiments are contemplated. Accordingly, it is not intended that the disclosure is limited in its scope to the details of construction and arrangement of components set forth in the following description or illustrated in the drawings. Other embodiments of the disclosure are capable of being practiced or carried out in various ways. Also, in describing the embodiments, specific terminology will be resorted to for the sake of clarity. It is intended that each term contemplates its broadest meaning as understood by those skilled in the art and includes all technical equivalents which operate in a similar manner to accomplish a similar purpose.

It should also be noted that, as used in the specification and the appended claims, the singular forms "a," "an," and "the" include plural references unless the context clearly dictates otherwise. References to a composition containing "a" constituent is intended to include other constituents in addition to the one named.

Ranges may be expressed herein as from "about" or "approximately" or "substantially" one particular value and/or to "about" or "approximately" or "substantially" another particular value. When such a range is expressed, other exemplary embodiments include from the one particular value and/or to the other particular value.

Herein, the use of terms such as "having," "has," "including," or "includes" are open-ended and are intended to have the same meaning as terms such as "comprising" or "comprises" and not preclude the presence of other structure, material, or acts. Similarly, though the use of terms such as "can" or "may" are intended to be open-ended and to reflect that structure, material, or acts are not necessary, the failure to use such terms is not intended to reflect that structure, material, or acts are essential. To the extent that structure, material, or acts are presently considered to be essential, they are identified as such.

It is also to be understood that the mention of one or more method steps does not preclude the presence of additional method steps or intervening method steps between those steps expressly identified. Moreover, although the term "step" may be used herein to connote different aspects of methods employed, the term should not be interpreted as implying any particular order among or between various steps herein disclosed unless and except when the order of individual steps is explicitly required.

The components described hereinafter as making up various elements of the disclosure are intended to be illustrative and not restrictive. Many suitable components that would perform the same or similar functions as the components described herein are intended to be embraced within the scope of the disclosure. Such other components not described herein can include, but are not limited to, for example, similar components that are developed after development of the presently disclosed subject matter. Additionally, the components described herein may apply to any other component within the disclosure. Merely discussing a feature or component in relation to one embodiment does not preclude the feature or component from being used or associated with another embodiment.

To facilitate an understanding of the principles and features of the disclosure, various illustrative embodiments are explained below. Referring to FIG. 1A there is a schematic perspective representation of an illustrative embodiment of the present invention. Presented is an IPL device 2 comprising a housing/body 4 configured to be received in the hand of a user. The device connects to a mains power source via cord 6 and comprises a user operated trigger in the form of a push button 8 for causing operation. A vent 10 is provided in the housing for exhausting hot air. At a forward end 11 of the housing 4 a head 12 is shown mounted relative to the housing 4. The head comprises a rearward end 14*a* configured to mount and demount relative to the housing 4 and a forward end 14*b* defining a (second) skin contact surface 16 in the form of a peripheral rim surrounding an output window 18 through which light energy pulses are transmitted. The output window 18 is an opening into the head 12, specifically into a secondary lightguide 20 typically in the form of a channel comprising aluminum channel walls for directing the light energy pulses through the output window 18 and onto the skin of a user. The channel may comprise a through-bore extending through the entirety of the head from the forward to a rearward ends 14*b*, 14*a*. One or more sensors are provided in the skin contact surface 16 for determining contact with the skin of a user, from which an output is transmitted to the control system for controlling operation of the device 2. With the head 12 mounted to the housing 4, the device is operable in a configuration where there is no physical contact of the leading end of the body 4 with the user's skin, rather it is the peripheral rim of the head that contacts the skin.

Figure 1B:
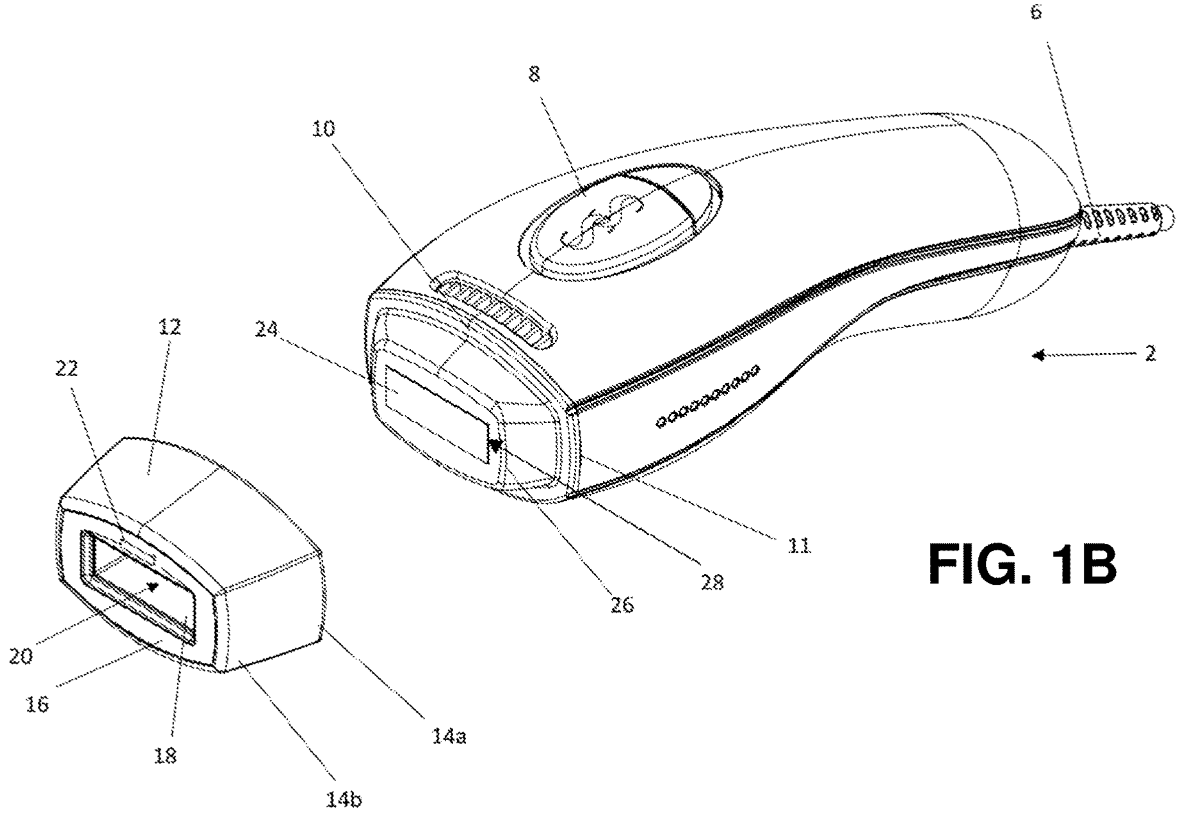

Referring now to FIG. 1B, the head 12 is demounted from the housing 4. The device 2 is therefore operable in a first operable configuration without the presence of the head 12. The forward end of the housing 4 is shaped to receive the head 12 and comprises a primary lightguide 24 comprising a material 26 having a first skin contact surface 28. In operation, the first skin contact surface 28 of the material 26 communicates with the skin and provides a cooling effect as described further with respect to FIGS. 2A, 2B.

Figure 2A:
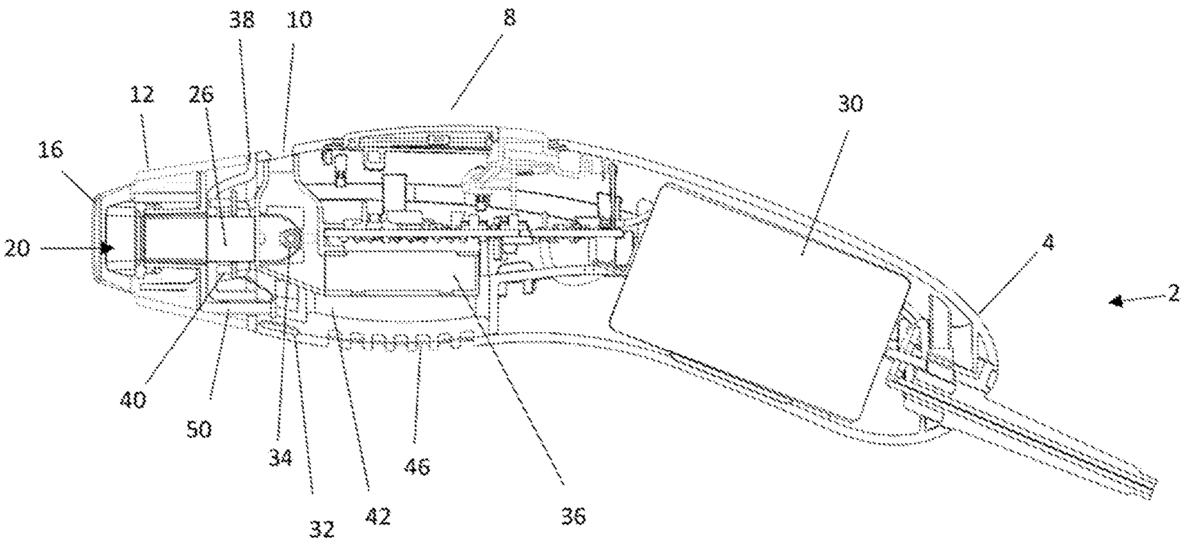
FIGS. 2A, 2B are schematic cross sectional views of a device according to an illustrative embodiment of the present invention with a head attached in FIG. 2A and detached in FIG. 2B.
Figure 2B:
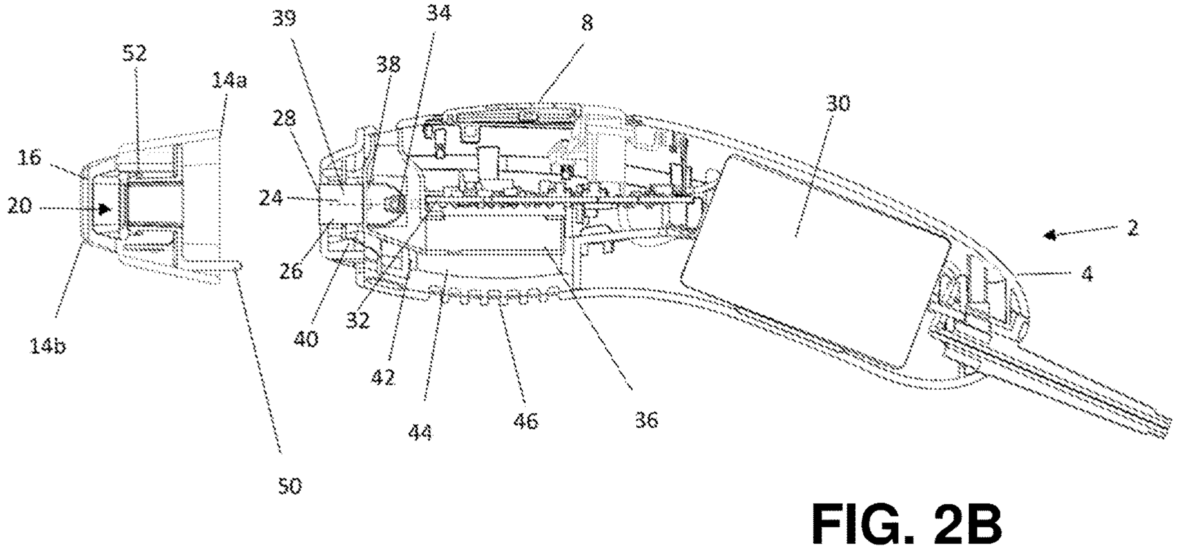

Referring now to FIGS. 2A, 2B, cross sectional views of an illustrative embodiment of the present invention is presented with the head 12 in communication with the housing 4 (FIG. 2A) and with the head 12 removed from the housing 4 (FIG. 2B). The device comprises a charge storage device 30 in the form of a capacitor and a control system 32 for controlling operation of the device including discharge of the capacitor over the flashlamp 34. Further provided is a fan 36 for directing cooling air across the flashlamp 34 and out of the vent 10. Referring to FIG. 2B, the primary lightguide represented by a dashed line 24 is defined between the flashlamp 34 and the first skin contact surface 28. The primary lightguide 24 comprises the solid material 26 typically comprising glass or sapphire having at a trailing edge a filter 38 which may be a coating on the material 26 for filtering most harmful wavelengths of light in the UV and blue wavelength ranges that are inherently emitted by the flashlamp 34. The primary lightguide comprises a light reflective wall defining a channel 39 in which is positioned the solid material 26. The solid material 26 abuts against the wall meaning light energy pulses must travel through the solid material.

During operation of the device in a first operable configuration with the head 12 demounted from the housing 4 the solid material 26 will heat up due to transmission losses and conduction during the emission of each energy pulse from the flashlamp 34. Without cooling the material 26 it is likely that the material may reach a temperature painful or harmful to the skin. The device 2 therefore further comprises a cooling arrangement for cooling the material 26 in the form of a Thermoelectric Cooling System (TEC) comprising a thermoelectric cooler such as a peltier 40, heat pipes 42 and heat exchanger 44. The fan 36 drives air across the heat exchanger 44. Air inlet 46 is provided in the housing for enabling passage of cooling air to the heat exchanger 44. A significant benefit of utilizing a solid material 26 is that it may be cooled to a temperature below normal skin temperature which means the skin contact surface 28 of the material 26 cools the skin which is particularly beneficial for sensitive treatment areas such as underarm and bikini areas.

The rearward end 14*a* of the head 12 is configured to be mounted to the leading portion of the housing 4 through a connector 50. In the illustrative embodiment the connector 50 extends outwardly from the rearward end 14*a* of the head 12 and seats into a corresponding opening in the forward end of the housing 4. Engagement between the connector 50 and the housing couples the head 12 to the housing 4. Additional or alternative connections may be provided for enabling engagement such as mechanical or magnetic attachment mechanisms. Electronics present in the head (as described further below) are coupled to the control system with the head mounted by the connector 50.

The device is capable of determining that the head is mounted to the body and/or that the head is detached from the body and operation of the device is modified. This may be achieved for example by a sensor output or the detection of an electrical connection between electronics provided in the head. The operative parameter is typically power, and the control system enables a higher output power output with the head mounted compared to the optical power output with the head demounted. In the first operable configuration with the head detached, as an example the optical power is at a reduced value of 6 W. To produce this power the optical power may be output at 18 J and three seconds between flashes, where 18 J may be 6 J/cm$^2$ for a 3 cm$^2$ treatment area. The TEC is operational at a suitable power to control the temperature of the solid material 26 such that the skin contact surface 28 cools the skin. In the second operative configuration with the head mounted to the housing, a relatively high optical power can be output. For example, 20 W may be produced by 18 J and 0.9 seconds between flashes, where 18 J may again be 6 J/cm$^2$ for a 3 cm$^2$ treatment area. In this second operational configuration, the TEC may be switched off or operated at reduced power (compared to the optical power) due to the spacing of the first skin contact surface 28 from the skin.

Referring back to FIGS. 2A, 2B, the head 12 defines the second skin contact surface 16 which sits against the skin in use. The secondary lightguide is defined between the first skin contact surface 28 and the second skin contact surface 16. The secondary lightguide comprises a reflective wall 52 defining a channel or pathway for the light energy pulses. The channel is an airgap, and the secondary lightguide may be termed a light pipe. Typical lightguides comprise a reflective aluminum wall defining the channel, with no solid medium that can contact the skin. The second skin contact surface is the peripheral rim of the leading end of the head 12.

Figure 3A:
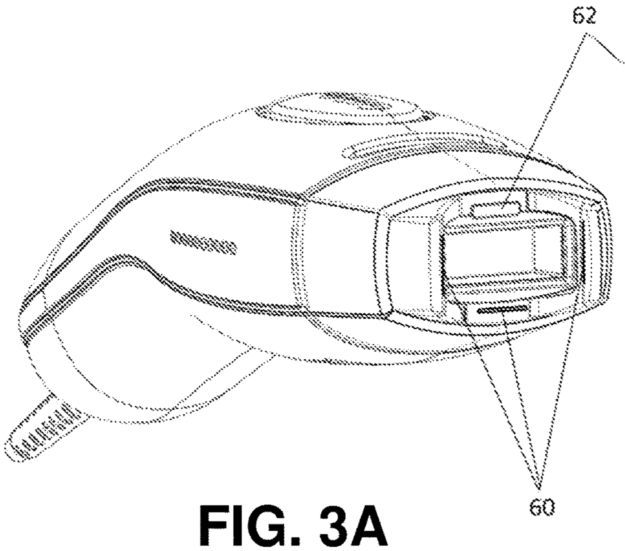
FIGS. 3A, 3B are schematic perspective views of a device according to an illustrative embodiment of the present invention with a head attached in FIG. 3A and detached in FIG. 3B.
Figure 3B:
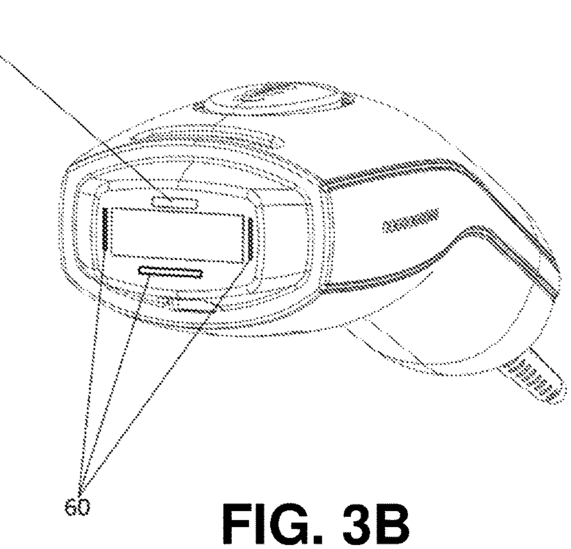

Referring now to FIGS. 3A, 3B, perspective representations of a device according to an illustrative embodiment of the invention is presented from a front view with the head 12 attached (FIG. 3A) and detached (FIG. 3B). It is important in devices according to the present invention that good skin contact is required before allowing emission of a pulse of energy from the flashlamp. Good contact can be defined as a condition where the light output area is sufficiently covered by skin that any stray optical radiation is below harmful levels. As such, safety features are implemented so that the device will not emit radiation unless the device is in contact with a user's skin to minimize stray optical radiation from the device in operation which may be at unsafe levels for the eyes. This is typically achieved through the provision of multiple sensors adjacent each side of the output window (for example above, below and to either side of a rectangular output window) in the head of the device where a surface must be detected by each sensor as a requirement for radiation to be emitted. If one sensor does not measure a threshold value, then it is determined by the control system of the device that there is no skin contact and firing is prevented. This is to prevent the device firing when good contact with the skin is not achieved with the associated risk of the emission of potentially harmful levels of stray optical radiation. Stray optical radiation can be defined as light emitted by the device that is intended to be absorbed by the target skin area for treatment purposes, but either misses the intended target, is reflected or remitted from the target. Various sensors may be utilized such as capacitive contact sensors or proximity sensors.

As shown in FIGS. 3A, 3B in either condition (with or without the head attached) there are multiple capacitive skin contact sensors 60 positioned around the peripheral edge of the exit of the first and secondary lightguides. The sensors 60 are positioned around the peripheral rim 16 of the head 14 are disposed around the skin contact surface 28 of the material 26 with the head 14 removed. Outputs from the sensors are received by the control system, and control of the device is dependent upon the sensor output. For example, assuming a threshold capacitance is measured from the sensors, then the control system in the device does not prevent emission of an energy pulse as it is deemed there is contact with the skin and emission of an energy pulse is safe. An additional sensor such as a skin tone sensor 62 (which may measure reflectance) may be provided and the control system may use this measurement both to control whether an energy pulse may be emitted and also be used to control the energy of the light energy pulse emitted dependent upon the reflectance (and therefore determined skin tone).

In an embodiment of the invention, the sensors 60/62 at the forward end of the housing that are described as being disposed around the peripheral edge of the output window are carried by a detachable cover, configured to connect to the control system and operate in the same way as described above.

Figure 4A:
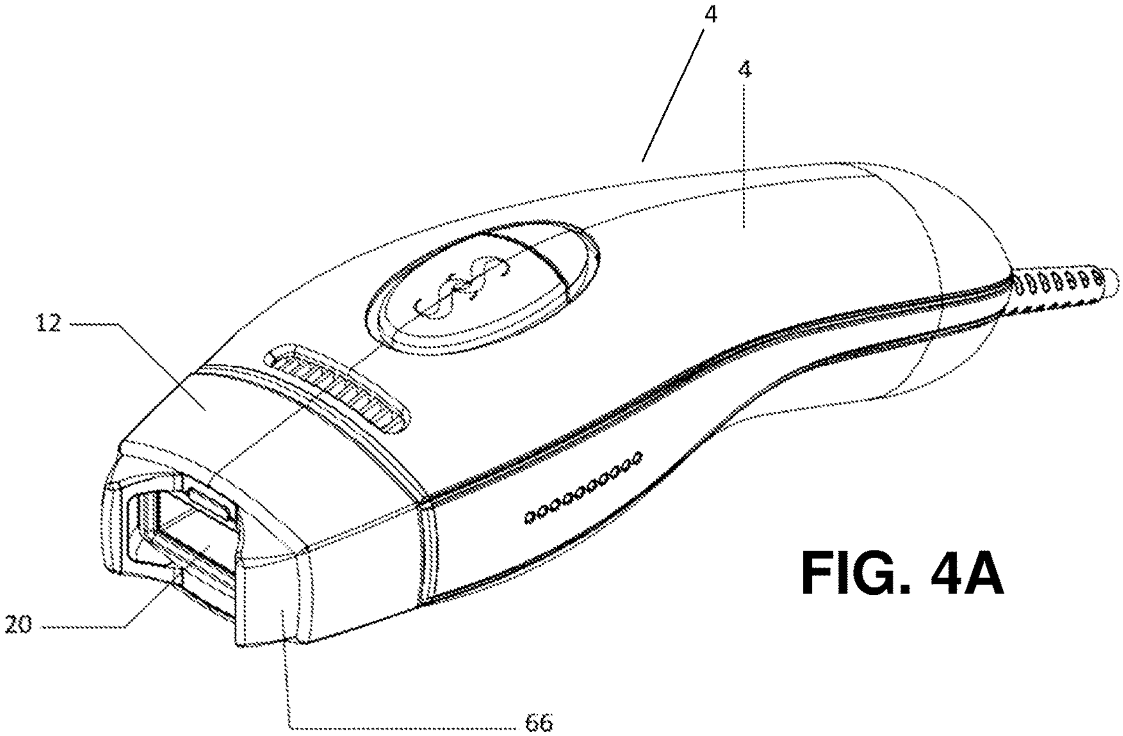
FIGS. 4A, 4B are schematic perspective views of a device according to an illustrative embodiment of the present invention with a head attached in FIG. 4A and detached in FIG. 4B.
Figure 4B:
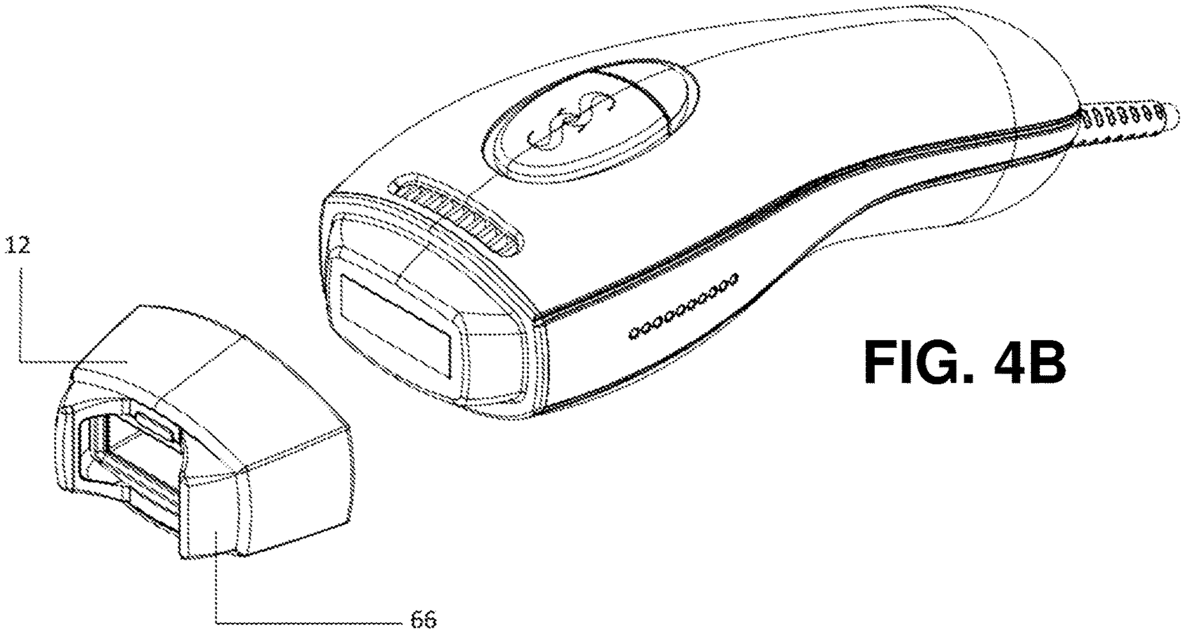

Referring now to FIGS. 4A, 4B, there are schematic perspective views of a device according to an illustrative embodiment of the present invention with a head attached in FIG. 4A and detached in FIG. 4B. In this illustrative embodiment (and as schematically also presented in FIG. 3A) at least a portion of the forward end of the head 12 may be moveable. The forward end of the head 12 comprises a second skin contact surface 16. At least a part of the forward end of the head having the skin contact surface may be at least partially moveable from a rest position to a deflected position in order to accommodate the geometry of the skin to be treated. This may be achieved through the provision for example of one or more projections (two shown in the illustrative embodiment) 66 configured to deflect independently of one another to conform to the geometry of the skin. Each of the projections carry a sensor 60/62. The or each projection 66 is configured to be received into a corresponding opening in the body of the head 12, where the projection in the rest position extends outwardly from the opening in the head body, and in the deflected position the projection is at least partially withdrawn into an opening in the head body. The at least one projection is beneficially biased to the rest position by a spring and are each pivotally mounted relative to the head 12 body.

The device according to any of the illustrative embodiments may be configured to monitor the temperature of the material 26 of the primary lightguide 24, and the control system may be configured to control operating parameters of the TEC dependent upon the measured values. A suitable temperature sensor may be utilized such as a thermocouple of resistive temperature measuring device. The control system 32 may be configured to control parameters of the TEC (such as the peltier current) to maintain a constant material temperature at the first skin contact surface 28 independent of the speed in which the user activates the device to effect emission of consecutive pulses. The temperature monitoring may also be used to control the optical power (through either modification of the time between discharge of consecutive light energy pulses or energy per pulse) to assist with reduction of waste heat generated in the device and allow the material 26 to cool further and faster. Additionally, the temperature monitoring may also be utilized such that the control system prevents emission of a light energy pulse unless the material 26 temperature is within a predetermined temperature range. This means that if the temperature is too high for safe treatment, then discharge of a light energy pulse is prevented. This may occur when the device is first switched on, or when transitioning from the second to the first operational configuration, particularly if the device was operating at high optical power in the second operable configuration.

Figure 5:
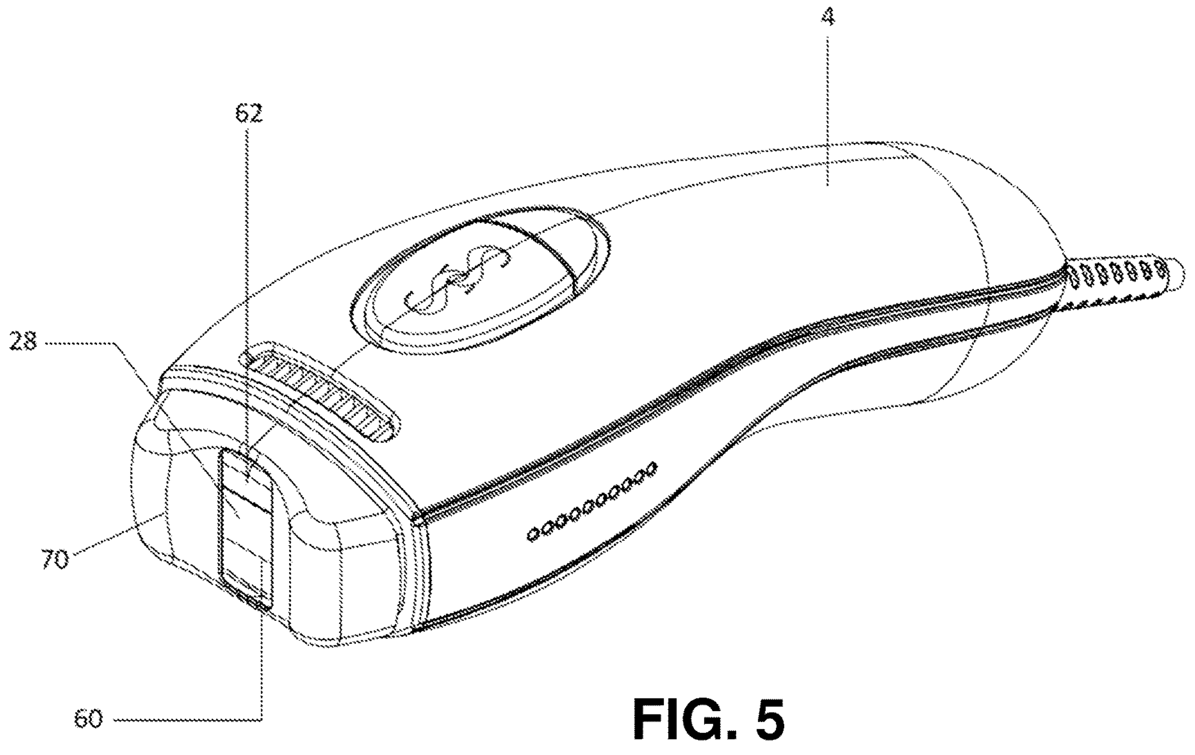
FIG. 5 is a schematic perspective view of a device according to an illustrative embodiment of the present invention with an adaptor.

Additional optional features according to illustrative embodiment of the present invention may be the provision of multiple different heads 12 with different cross-sectional areas of the light output window. Furthermore, as shown in FIG. 5, an adaptor 70 may be secured to the forward end of the housing 4 configured to reduce the first skin contact surface area 28. In such an embodiment the treatment area is reduced meaning that small areas, such as top lip can be treated with improved usability. Sensors 60 that are covered by the adaptor 70 are beneficially disabled in such a configuration.

It will be appreciated that in each of the illustrative embodiment the device is operable in at least two configurations, where the head 12 is either mounted to the housing 4 or is demounted from the housing 4. Accordingly, a significant advantage is provided in that a single device is reconfigurable depending on the area of the body in which the user wishes to treat. Therefore, the device 2 combines high power and speed of a Type 1 system with an increased safety and reduced pain of a Type 2 system in a single device without a corresponding increase in size, cost and weight.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way. Instead, it is intended that the invention is defined by the claims appended hereto.

What is claimed is:

1. A skin treatment device comprising:

a body;

a light source housed within the body and configured to deliver light energy pulses;

a primary lightguide configured to guide the light energy pulses from the light source, through a solid material of the primary lightguide, and onto a subject's skin, the solid material defining a first skin contact surface for providing contact with the subject's skin;

a cooling arrangement configured to cool the solid material;

a head comprising a secondary lightguide defining a light energy pulse transmission channel extending between a forward end of the head and a rearward end of the head, the head configured to be mountable to and demountable from the body; and a control system configured to:

control delivery of multiple light energy pulses;

control delivery of an optical power output defined as light output energy per pulse emitted from the skin treatment device divided by the time between consecutive pulses; and cause modification to the optical power output dependent upon whether the head is mounted to or demounted from the body;

wherein:

the skin treatment device is configured to be operable in a first operable configuration with the head demounted from the body and in a second operable configuration where the head is mounted to the body;

in the second operable configuration, the first skin contact surface is spaced apart from the subject's skin and the light energy pulses pass through both the solid material of the primary lightguide and the light energy pulse transmission channel of the secondary lightguide of the head;

the forward end of the head comprises a second skin contact surface:

defining an opening to the light energy pulse transmission channel; and extending around at least a part of a periphery of the opening;

the rearward end of the head extends to the forward end of the head; and the optical power output is greater when the head is mounted to the body than when the head is demounted from the body.

2. The device according to claim 1 further comprising:

a temperature sensor configured to measure a temperature of the solid material;

wherein the control system is further configured to control operating parameters of the cooling arrangement dependent upon the measured temperature of the solid material.

3. The skin treatment device according to claim 1 further comprising:

a detector for detecting whether the head is mounted to or demounted from the body.

4. The device according to claim 1 further comprising:

an adaptor for securing to the body and arranged to partially obscure the first skin contact surface.

5. The skin treatment device according to claim 1, wherein:

the skin treatment device is further configured to detect whether the head is mounted to or demounted from the body; and the control system is further configured to modify operation of the skin treatment device dependent on the whether the head is mounted to or demounted from the body.

6. The skin treatment device according to claim 1, wherein:

the skin treatment device is further configured to detect whether the head is mounted to or demounted from the body; and the control system is further configured to:

control a time period between delivery of consecutive pulses; and select the time period from a plurality of different time periods dependent upon whether the head is mounted to or demounted from the body.

7. The skin treatment device according to claim 1, wherein the solid material comprises glass or sapphire.

8. The skin treatment device according to claim 1, wherein the primary lightguide further comprises a filter configured to filter out predetermined wavelengths of the light energy pulses.

9. The skin treatment device according to claim 1, wherein a majority of the light energy pulse transmission channel comprises a through-bore.

10. The device according to claim 1, wherein the second skin contact surface is further defined by a peripheral rim extending around the opening to the light energy pulse transmission channel of the secondary lightguide.

11. The device according to claim 1, wherein the cooling arrangement is a Thermoelectric Cooling System (TEC).

12. The device according to claim 1, wherein the cooling arrangement is activated in both the first and second operable configurations.

13. The device according to claim 1, wherein:

the head further comprises sensors disposed adjacent the opening; and when in the second operable configuration, the control system is further configured to:

receive sensor outputs from the sensors; and based on the sensor outputs, control operation of the skin treatment device.

14. The device according to claim 1, wherein;

the body comprises sensors disposed adjacent the first skin contact surface; and when in the first operable configuration, the control system is further configured to:

receive sensor outputs from sensors; and based on the sensor outputs, control operation of the skin treatment device.

15. The device according to claim 1, wherein at least a portion of the forward end of the head is at least partially moveable from a rest position to a deflected position to accommodate the geometry of the subject's skin.

16. The device according to claim 1, further comprising:
a temperature sensor configured to measure a temperature of the solid material;
wherein the control system is further configured to reduce the optical power output if the measured temperature of the solid material reaches or exceeds a threshold value.

17. The device according to claim 1, further comprising:
a temperature sensor configured to measure a temperature of the solid material;
wherein the control system is further configured to prevent delivery of a light energy pulse if the measured temperature of the solid material reaches or exceeds a threshold value.

18. The skin treatment device according to claim 1, wherein the optical power output is between 1.5-3 times greater when the head is mounted to the body than when the head is demounted from the body.

19. The skin treatment device according to claim 6, wherein the time period is longer when the head is demounted from the body than when the head is mounted to the body.

20. The device according to claim 11, wherein the TEC comprises:
a thermoelectric cooler;
a heat exchanger;
a heat pipe between the thermoelectric cooler and the heat exchanger; and
a fan configure to direct air towards the heat exchanger.

21. A skin treatment device comprising:
a body;
a light source housed within the body and configured to deliver light energy pulses;
a primary lightguide configured to guide the light energy pulses from the light source, through a solid material of the primary lightguide, and onto a subject's skin, the solid material defining a first skin contact surface for providing contact with the subject's skin;
a cooling arrangement configured to cool the solid material;
a head comprising a secondary lightguide defining a light energy pulse transmission channel extending between a forward end of the head and a rearward end of the head, the head configured to be mountable to and demountable from the body; and
a control system configured to:
control delivery of multiple light energy pulses;
control a time period between delivery of consecutive pulses; and
select the time period from a plurality of different time periods dependent upon whether the head is mounted to or demounted from the body;
wherein:
the skin treatment device is configured to be operable in a first operable configuration with the head demounted from the body and in a second operable configuration where the head is mounted to the body;
in the second operable configuration, the first skin contact surface is spaced apart from the subject's skin and the light energy pulses pass through both the solid material of the primary lightguide and the light energy pulse transmission channel of the secondary lightguide of the head; and
the forward end of the head comprises a second skin contact surface:
defining an opening to the light energy pulse transmission channel; and
extending around at least a part of a periphery of the opening.

22. A skin treatment device comprising:
a body;
a light source housed within the body and configured to deliver light energy pulses;
a primary lightguide configured to guide the light energy pulses from the light source, through a solid material of the primary lightguide, and onto a subject's skin, the solid material defining a first skin contact surface for providing contact with the subject's skin;
a cooling arrangement configured to cool the solid material;
a head comprising a secondary lightguide defining a light energy pulse transmission channel extending between a forward end of the head and a rearward end of the head, the head configured to be mountable to and demountable from the body; and
a control system configured to:
control delivery of multiple light energy pulses;
control delivery of an optical power output defined as light output energy per pulse emitted from the skin treatment device divided by the time between consecutive pulses; and
cause modification to the optical power output dependent upon whether the head is mounted to or demounted from the body;
wherein:
the skin treatment device is configured to be operable in a first operable configuration with the head demounted from the body and in a second operable configuration where the head is mounted to the body;
in the second operable configuration, the first skin contact surface is spaced apart from the subject's skin and the light energy pulses pass through both the solid material of the primary lightguide and the light energy pulse transmission channel of the secondary lightguide of the head;
the forward end of the head comprises a second skin contact surface:
defining an opening to the light energy pulse transmission channel; and
extending around at least a part of a periphery of the opening; and
the optical power output is between 1.5-3 times greater when the head is mounted to the body than when the head is demounted from the body.

* * * * *